United States Patent [19]

Sakakibara et al.

[11] Patent Number: 4,920,022

[45] Date of Patent: Apr. 24, 1990

[54] ELECTROPHOTOGRAPHIC PHOTOSENSITIVE MEMBER COMPRISING ARYL AMINE CHARGE TRANSPORT MATERIAL

[75] Inventors: Teigo Sakakibara, Tokyo; Kiyoshi Sakai, Chofu; Harumi Sakoh, Tokyo; Shoji Amamiya, Sagamihara, all of Japan

[73] Assignee: Canon Kabushiki Kaisha, Tokyo, Japan

[21] Appl. No.: 345,236

[22] Filed: May 1, 1989

[30] Foreign Application Priority Data

May 7, 1988 [JP]  Japan .................................. 63-111250
May 7, 1988 [JP]  Japan .................................. 63-111255

[51] Int. Cl.$^5$ .............................................. G03G 5/14
[52] U.S. Cl. ........................................ 430/59; 430/73; 252/500; 564/309

[58] Field of Search .................... 430/58, 73, 74, 59; 564/309; 282/500

[56] References Cited

U.S. PATENT DOCUMENTS

| | | | |
|---|---|---|---|
| 4,140,529 | 2/1979 | Pai | 430/59 |
| 4,304,829 | 12/1981 | Limburg | 430/59 |
| 4,588,666 | 5/1986 | Stolka | 564/309 |
| 4,725,518 | 2/1988 | Carmichael | 430/58 |

*Primary Examiner*—J. David Welsh
*Attorney, Agent, or Firm*—Fitzpatrick, Cella, Harper & Scinto

[57] ABSTRACT

An electrophotographic photosensitive member comprises a conductive support and provided thereon a photosensitive layer, wherein said photosensitive layer contains an amine compound represented by the Formula (I) or Formula (II).

6 Claims, No Drawings

ELECTROPHOTOGRAPHIC PHOTOSENSITIVE MEMBER COMPRISING ARYL AMINE CHARGE TRANSPORT MATERIAL

BACKGROUND OF THE INVENTION

1. Field of the Invention

The present invention relates to an electrophotographic photosensitive member, and more particularly to an electrophotographic photosensitive member comprising a low-molecular organic photoconductive material that can impart improved electrophotographic characteristics.

2. Related Background Art

Inorganic photoconductive materials such as selenium, cadmium sulfide and zinc sulfide have been hitherto known as photoconductive materials used in electrophotographic photosensitive members. These photoconductive materials have a number of advantages, for example, that they can be electrostatically charged to a suitable potential in the dark, cause less charge loss in the dark, and can rapidly release charges as a result of irradiation by light, but, on the other hand, have various disadvantages. For example, in selenium photosensitive members, they may be readily crystallized by the factors such as temperature, humidity, dust and pressure, and, in particular, exceedingly crystallized at an atmospheric temperature more than 40° C., resulting in a lowering of chargeability, or generation of white dotts on an image. In cadmium sulfide photosensitive members, no stable sensitivity can be obtained in a highly humid environment. In zinc oxide photosensitive members, they require a sensitization effect attributable to sensitizing coloring matters as typified by Rose Bengale, but, since such sensitizing coloring matters bring about charge deterioration caused by corona charging or color-fading by light, can not provide stable images over a long period of time, disadvantageously.

On the other hand, various types of organic photoconductive polymers including polyvinyl carbazole have been hitherto proposed. These polymers, however, have been put into practical use with difficulty up to the present, notwithstanding their superiority to inorganic photoconductive materials in respect of film-forming properties and lightness in weight. This is because they have achieved no sufficient film-forming properties and also are inferior to the inorganic photoconductive materials in respect of sensitivity, durability, and stability against environmental changes. Also proposed are low-molecular organic photoconductive materials such as hydrazone compounds as disclosed in U.S. Pat. No. 4,150,987, triarylpyrazoline compounds as disclosed in U.S. Pat. No. 3,837,851, and 9-styryl anthracene compounds as disclosed in Japanese Patent Laid-open Application No. 51-94828 and Japanese Patent Laid-open Application No. 51-94829. Such low-molecular organic photoconductive materials have become able to eliminate the disadvantage in film-forming properties that has been questioned in the field of organic photoconductive polymers, by appropriately selecting binders to be used. They, however, can not be said to be satisfactory in respect of the sensitivity.

Under such circumstances, a laminated structure comprising a photosensitive layer functionally separated into a charge generation layer and a charge transport layer has been proposed in recent years. Electrophotographic photosensitive members employing this laminated structure as the photosensitive layer have become able to improve the sensitivity, charge retension, surface strength, etc. to visible light. Such electrophotographic photosensitive members are disclosed, for example, in U.S. Pat. Nos. 3,837,851 and 3,871,882.

However, in the electrophotographic photosensitive members employing the conventional low-molecular organic photoconductive material in the charge transport layer, the sensitivity is not necessarily satisfactory, and, in particular, light portion potential and dark portion potential may greatly fluctuate when charging and exposure to light are repeatedly carried out. Thus, there is a room for improvement.

SUMMARY OF THE INVENTION

An object of the present invention is to provide an electrophotographic photosensitive member having a satisfactory sensitivity and suffering less potential fluctuation even by repeated used.

Another object of the present invention is to provide an electrophotographic photosensitive member that employs a superior charge-transporting material in a laminate type function-separated photosensitive layer.

According to the present invention, there is provided an electrophotographic photosensitive member comprising a conductive support and provided thereon a photosensitive layer, wherein said photosensitive layer contains an amine compound represented by the following Formula (I) or Formula (II).

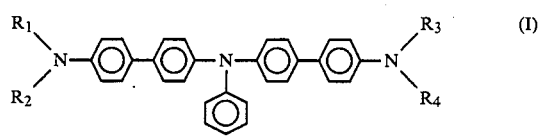

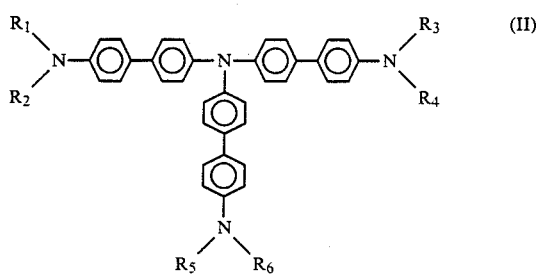

wherein $R_1$, $R_2$, $R_3$, $R_4$, $R_5$ and $R_6$ each represent an alkyl group such as methyl, ethyl, propyl, butyl and the like, an aralkyl group such as benzyl, phenethyl, naphthylmethyl and the like, or an aryl group such as phenyl, biphenyl, naphthyl and the like.

DESCRIPTION OF THE PREFERRED EMBODIMENTS

The above alkyl group, aralkyl group and aryl group may have substituents. The substituents of these include a halogen atom such as fluorine, chlorine, bromine iodine and the like, an alkyl group such as methyl, ethyl, propyl butyl and the like, an alkoxy group such as methoxy, ethoxy propoxy and the like, a phenyloxy group, or a substituted amino group such as dimethylamino, diethylamino, diphenylamino, ditolylamino, dimethoxyphenylamino, piperidino piperadino and the like.

Typical examples of the compounds respectively represented by Formulas (I) and (II) are set out below.

Exemplary Compounds:

I-1
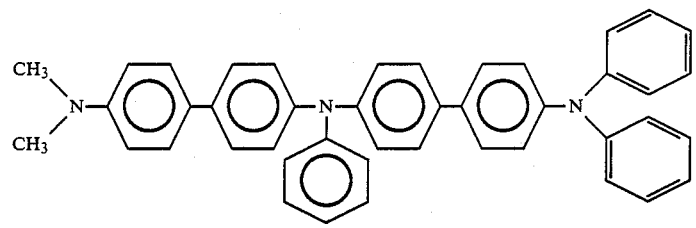
I-2
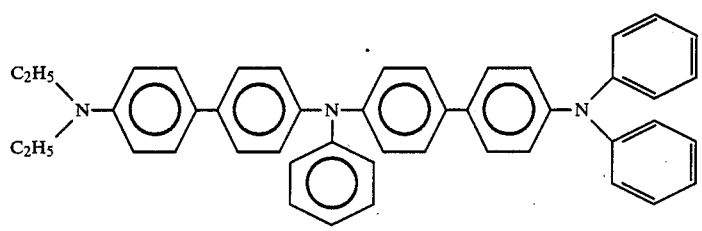
I-3
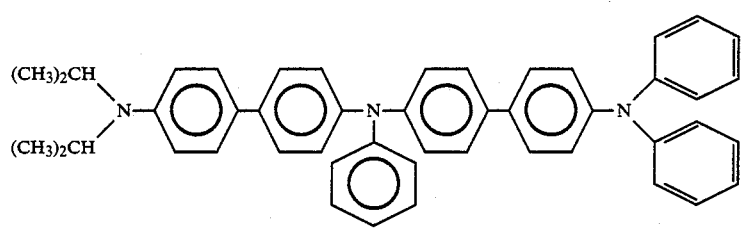
I-4
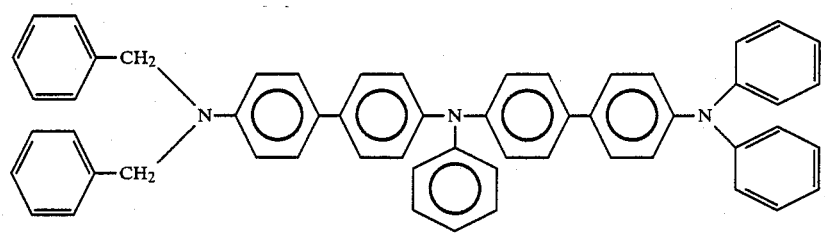
I-5
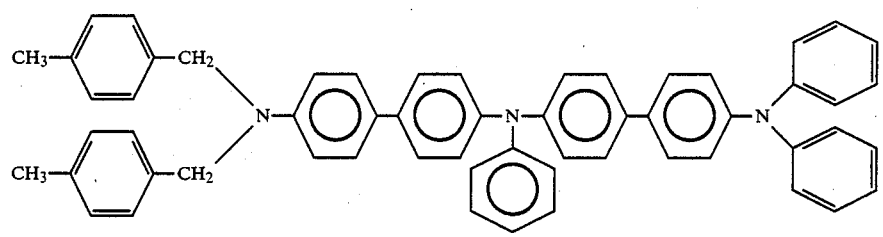
I-6
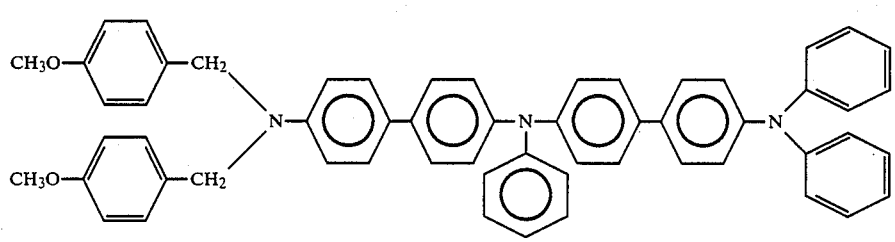

-continued
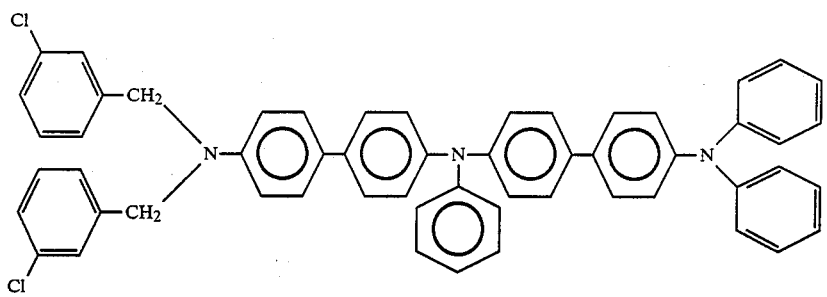
I-7
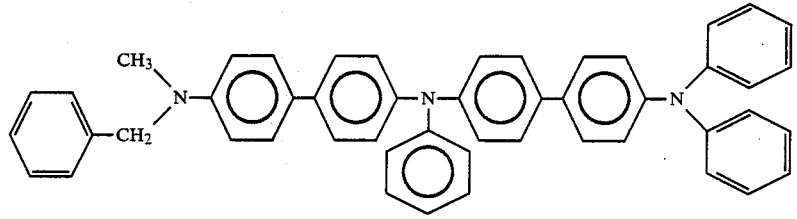
I-8
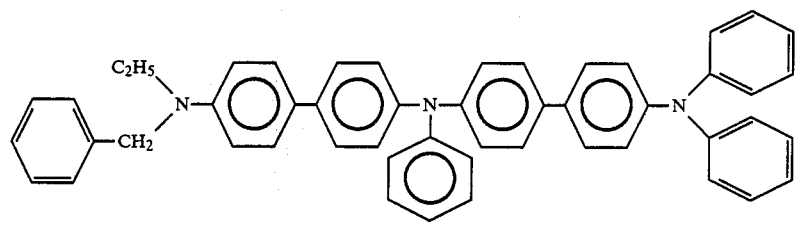
I-9
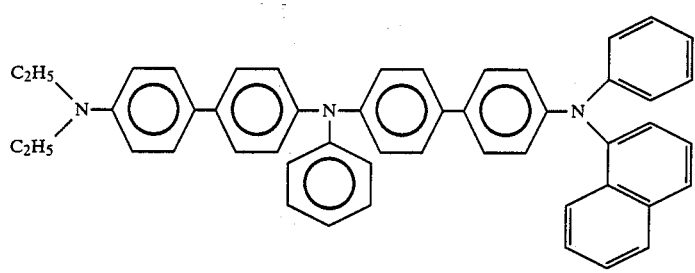
I-10
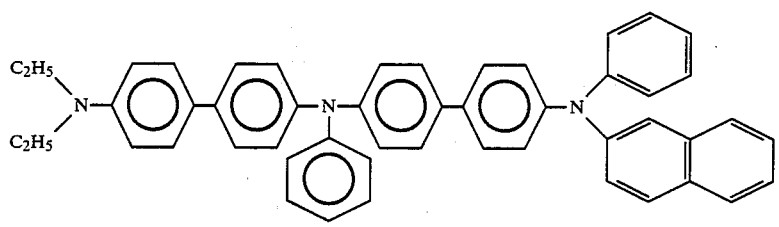
I-11
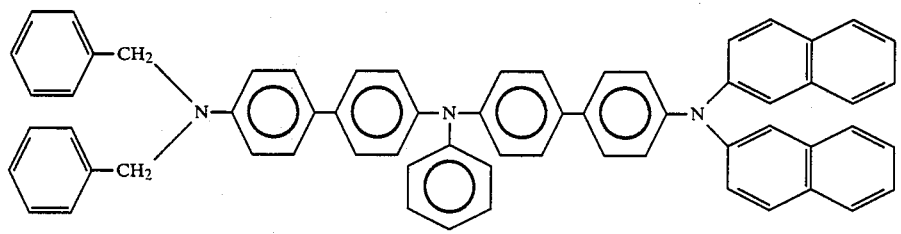
I-12

-continued
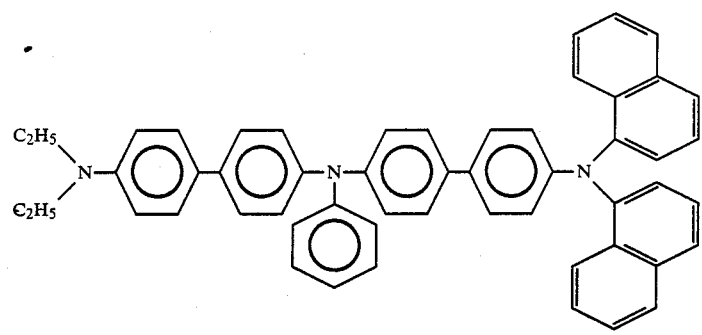
I-13
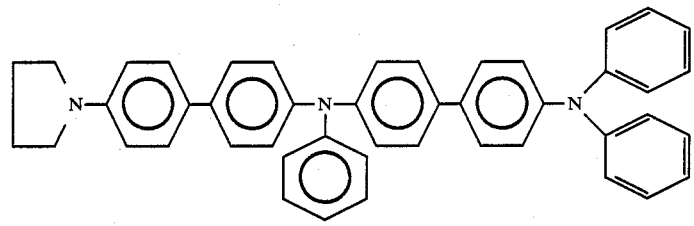
I-14
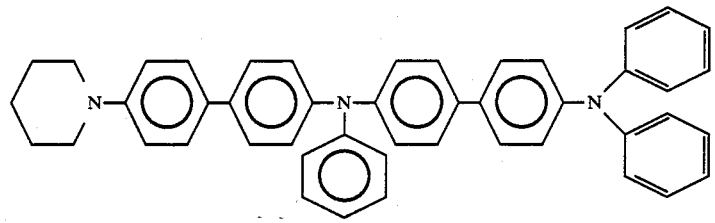
I-15
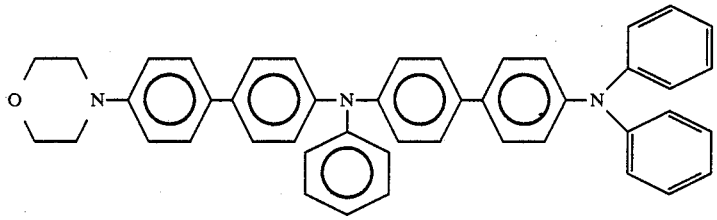
I-16
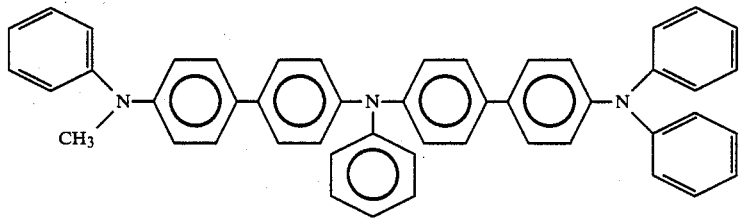
I-17
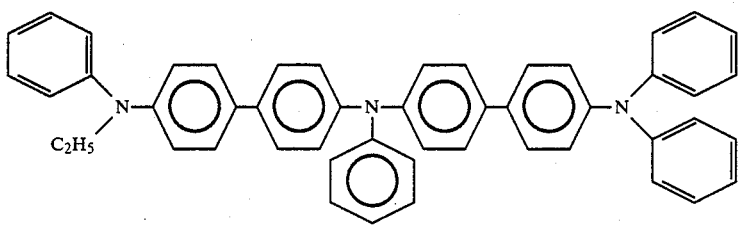
I-18

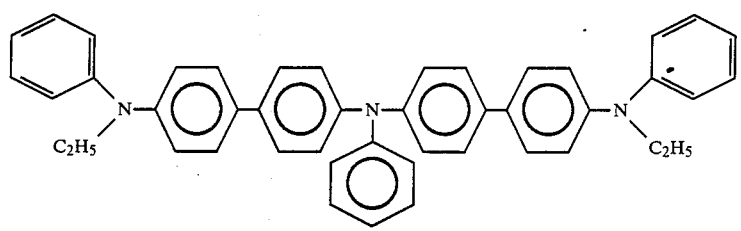
I-19
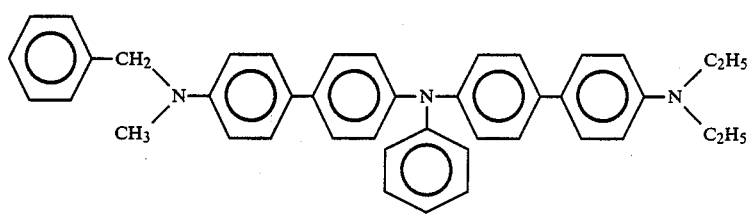
I-20
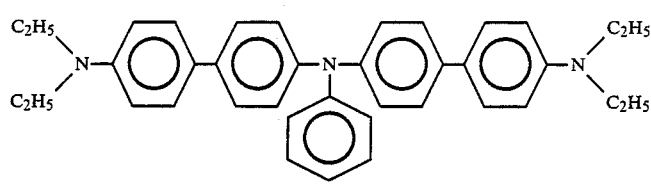
I-21
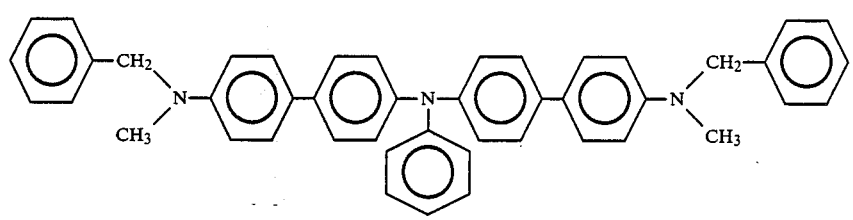
I-22
| No. | R₁— | R₂— | R₃— | R₄— | R₅— | R₆— |
|---|---|---|---|---|---|---|
| II-1 | CH₃— | CH₃— | C₆H₅— | C₆H₅— | C₆H₅— | C₆H₅— |
| II-2 | C₂H₅— | C₂H₅— | C₆H₅— | C₆H₅— | C₆H₅— | C₆H₅— |
| II-3 | C₂H₅— | C₂H₅— | C₂H₅— | C₂H₅— | C₆H₅— | C₆H₅— |
| II-4 | CH₃— | CH₃— | C₂H₅— | C₂H₅— | C₆H₅— | C₆H₅— |
| II-5 | CH₃— | CH₃— | C₂H₅— | C₆H₅— | C₆H₅— | C₆H₅— |
| II-6 | CH₃— | CH₃— | CH₃— | C₆H₅—CH₂— | C₆H₅— | C₆H₅— |
| II-7 | CH₃— | CH₃— | C₂H₅— | C₆H₅—CH₂— | C₆H₅— | C₆H₅— |
| II-8 | C₂H₅— | C₂H₅— | C₂H₅— | C₂H₅— | C₆H₅— | naphthyl— |

-continued

| No. | R₁— | R₂— | R₃— | R₄— | R₅— | R₆— |
|---|---|---|---|---|---|---|
| II-9 | CH₃— | CH₃— | CH₃—O—C₆H₄— | CH₃—O—C₆H₄— | C₂H₅— | C₂H₅— |
| II-10 | C₂H₅— | C₂H₅— | CH₃—C₆H₄— | CH₃—C₆H₄— | CH₃—C₆H₄— | CH₃—C₆H₄— |
| II-11 | CH₃— | CH₃— | (CH₃)₂CH— | (CH₃)₂CH— | C₆H₅— | C₆H₅— |
| II-12 | C₆H₅— | C₆H₅— | C₆H₅— | C₆H₅— | C₆H₅— | C₆H₅— |
| II-13 | C₂H₅— | C₂H₅— | C₂H₅— | C₂H₅— | C₂H₅— | C₂H₅— |
| II-14 | C₂H₅— | C₂H₅— | C₆H₅—CH₂— | C₆H₅—CH₂— | naphthyl— | naphthyl— |
| II-15 | Cl-C₆H₄— | Cl-C₆H₄— | C₆H₅— | C₆H₅— | CH₃— | CH₃— |
| II-16 | C₆H₅—CH₂CH₂— | C₆H₅—CH₂CH₂— | Br-C₆H₄— | Br-C₆H₄— | CH₃—C₆H₄— | CH₃—C₆H₄— |

The amine compound represented by the above Formula (I) can be readily synthesized, in general, by reacting amine

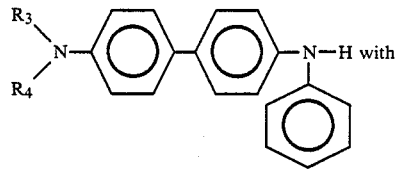

with

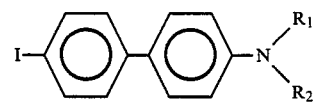

in equimolar amounts according to Ullmann reaction.

The amine compound represented by the above Formula (II) can also be readily synthesized, in general, by reacting amine

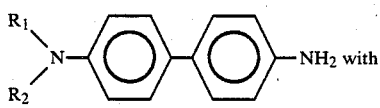

with

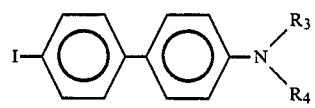

in equimolar amounts according to Ullmann reaction to separate the following intermediate:

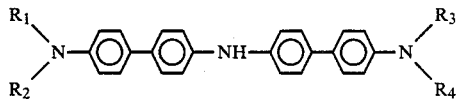

and again reacting this intermediate with

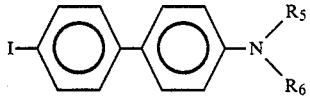

in equimolar amounts according to Ullmann reaction.

In a preferred embodiment of the present invention, the amine compounds represented by the above general formulae can be used in the charge-transporting material of the electrophotographic photosensitive member comprising a photosensitive layer functionally separated into a charge generation layer and a charge transport layer.

The charge transport layer according to the present invention may preferably be formed by coating a solution obtained by dissolving any of the compounds represented by the above general formulae and a binder in a suitable solvent, followed by drying. The binder used here may include, for example, polyacrylate resins, polysulfone resins, polyamide resins, acrylic resins, acrylonitrile resins, methacrylic resins, polyvinyl chloride resins, vinyl acetate resins, phenolic resins, epoxy resins, polyester resins, alkyd resins, polycarbonates, and polyurethanes, or copolymers containing at least two of the repeating units of these resins, as exemplified by a styrene/butadiene copolymer, a styrene/acrylonitrile copolymer and a styrene/maleic acid copolymer. In addition to insulating polymers like these, it is also possible to use organic photoconductive polymers such as polyvinyl carbazole, polyvinyl anthracene, polyvinyl pyrene and the like.

These binder and amine compound may be mixed preferably in such a proportion that the amine compound may comprise from 10 to 500 parts by weight based on 100 parts by weight of the binder.

The charge transport layer is electrically connected with the charge generation layer, and has functions to receive charge carriers injected from the charge generation layer in the presence of an electric field and transport the charge carriers to the surface. In this occasion, this charge transport layer may be laminated on the charge generation layer, or may otherwise be laminated beneath it. However, the charge transport layer may desirably laminated on the charge generation layer. This charge transport layer has a limit in the capability of transporting charge carriers, and therefore can not be made to have an unnecessarily large film thickness. In general, it may have a thickness of from 5 μm to 30 μm, but preferably in the range of from 8μm to 20 μm.

The organic solvent used when such a charge transport layer is formed may vary depending on the type of the binders to be used, and may preferably be selected from those which may not dissolve the charge generation layer and the subbing layer described below. Usable as specific organic solvents are alcohols such as methanol, ethanol, isopropanol and the like, ketones such as acetone, methyl ethyl ketone, cyclohexane and the like, amides such as N,N-diemthylformamide and the like, N,N-dimethylacetamide, sulfoxides such as dimethylsulfoxide and the like, ethers such as tetrahydrofuran, dioxane, ethylene glycol monomethyl ether and the like, esters such as methyl acetate, ethyl acetate and the like, aliphatic halogenated hydrocarbons such as chloroform, methylene chloride, dichloroethylene, carbon tetrachloride, trichloroethylene and the like, or aromatics such as benzene, toluene, xylene, monochlorobenzene, dichlorobenzene and the like.

The coating can be carried out by using coating methods such as dip coating, spray coating, Meyer bar coating, and curtain coating. The drying may preferably be carried out by a method comprising bringing a coating into dryness to the touch at room temperature followed by heat drying. The heat drying can be carried out generally at a temperature of from 30° C. to 200°C., in a period of time ranging from 5 minutes to 2 hours, and in still air or under air blow.

The charge transport layer can be made to contain various additives. Such additives may include diphenyl, diphenyl chloride, o-terphenyl, p-terphenyl, dibutyl phthalate, dimethylglycol phthalate, dioctyl phthalate, triphenylphosphoric acid, methylnaphthalene, benzopheneone, chlorinated paraffin, dilaurylthiopropionate, 3,5-dinitrosalicylic acid, and all sorts of fluorocarbons.

The charge generation layer used in the present invention can be used as a deposited layer or a resin-dispersed layer of the charge-generating materials such as selenium, selenium-tellurium, pyrylium, thiopyrylium or azulenium dyes, phthalocyanine pigments, anthanthrone pigments, dibenzpyrenequinone pigments, pyranthrone pigments, azo pigments, indigo pigments, quinacridone pigments, thiacyanines, asymmetric quinocyamines, quinocyamines, or amorphous silicon described in Japanese Patent Laid-open Application No. 55-143645.

Among these, particularly preferred are azo pigments or phthalocyanine pigments.

The charge-generating material used in the electrophotographic photosensitive member of the present invention may specifically include, for example, the following inorganic compounds or organic compound.

charge-generating materials:
III-(1) Amorphous silicon
III-(2) Selenium-tellurium

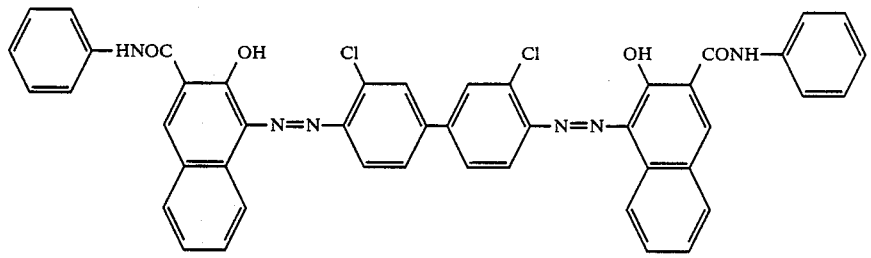

III-(3)

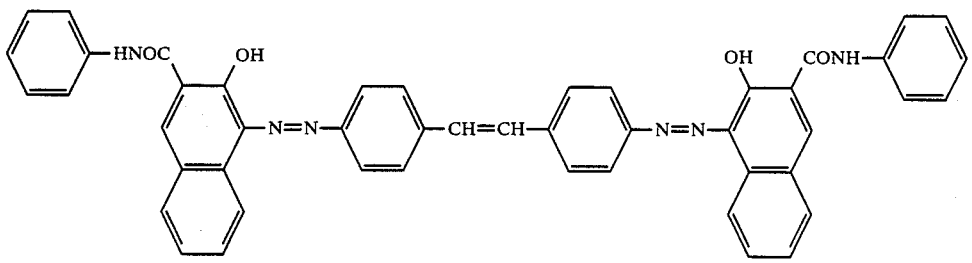

III-(4)

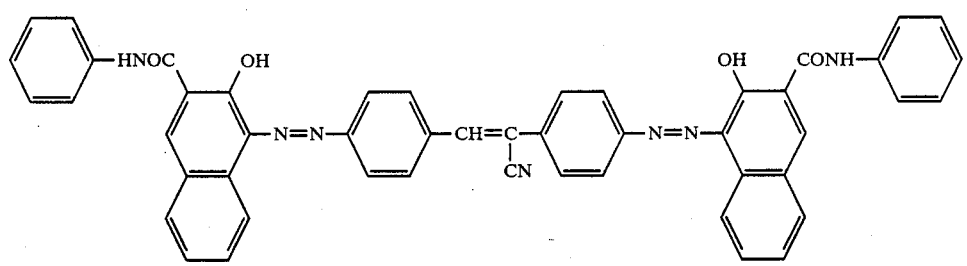
III-(5)
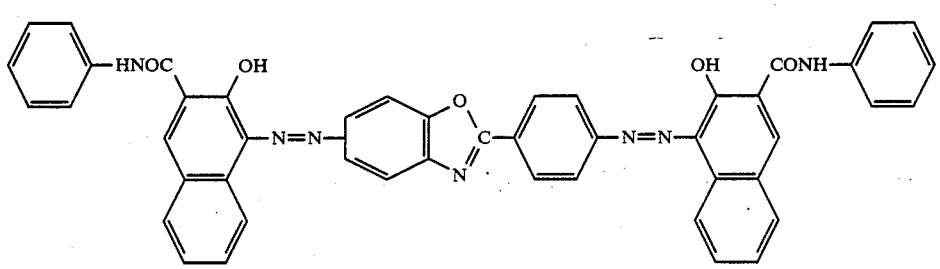
III-(6)
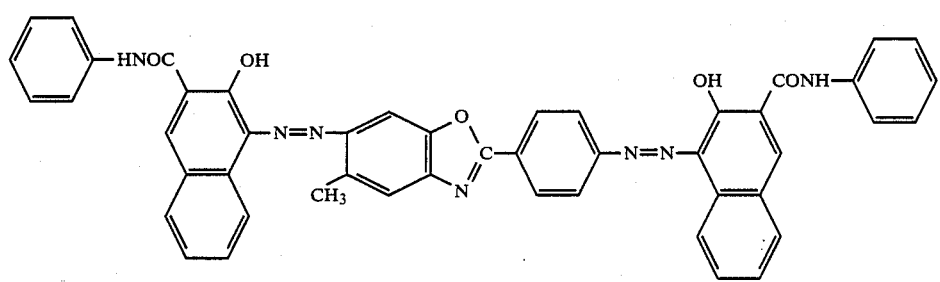
III-(7)
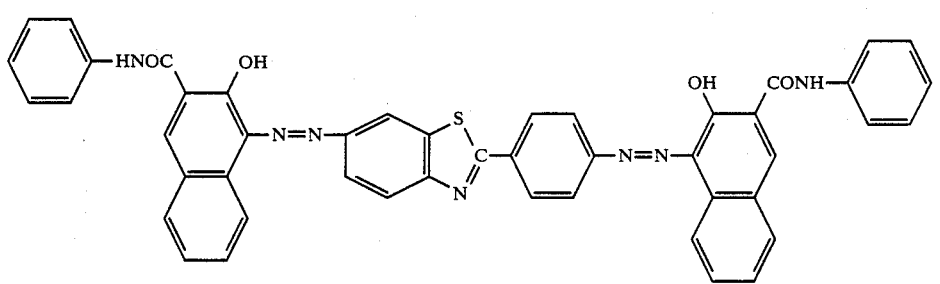
III-(8)
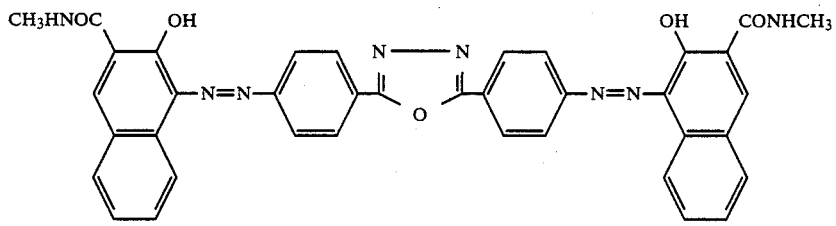
III-(9)
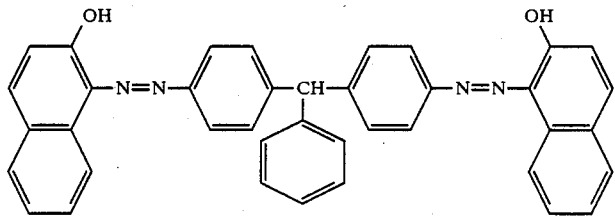
III-(10)

-continued
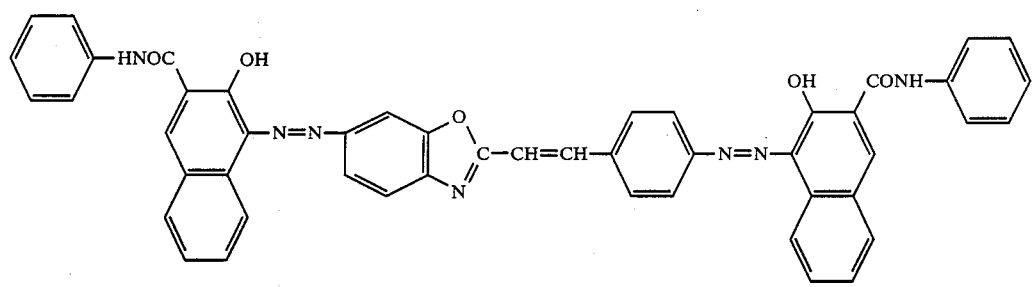
III-(11)
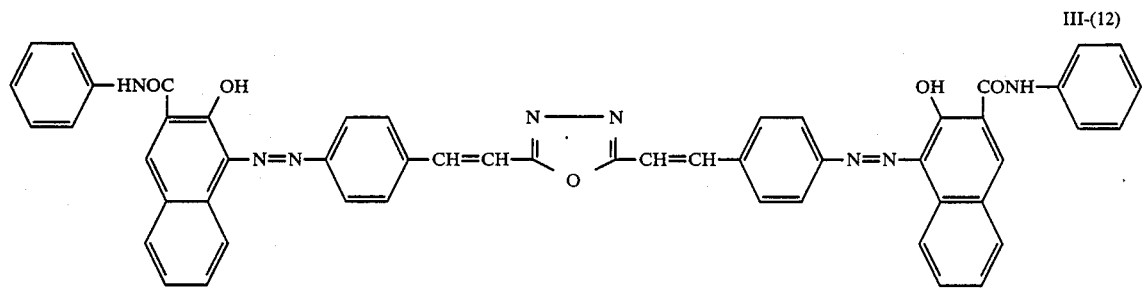
III-(12)
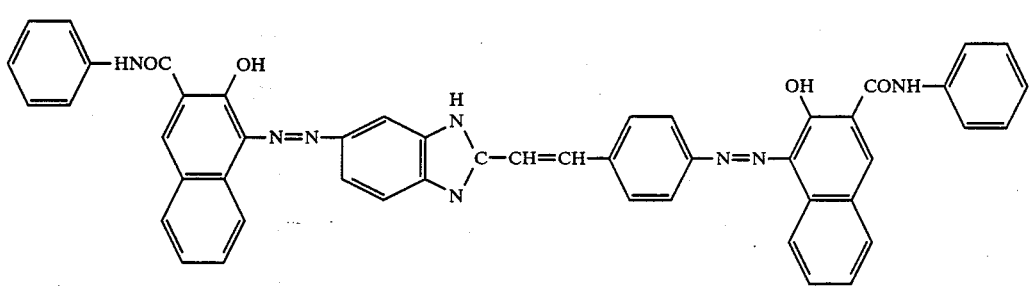
III-(13)
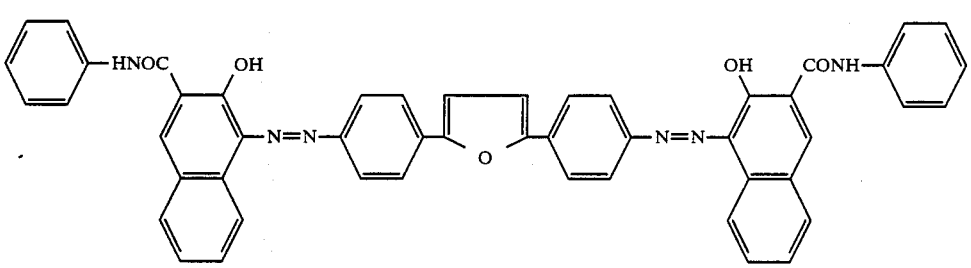
III-(14)
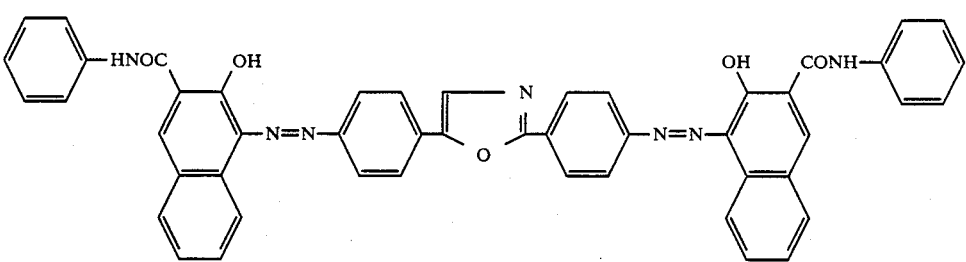
III-(15)
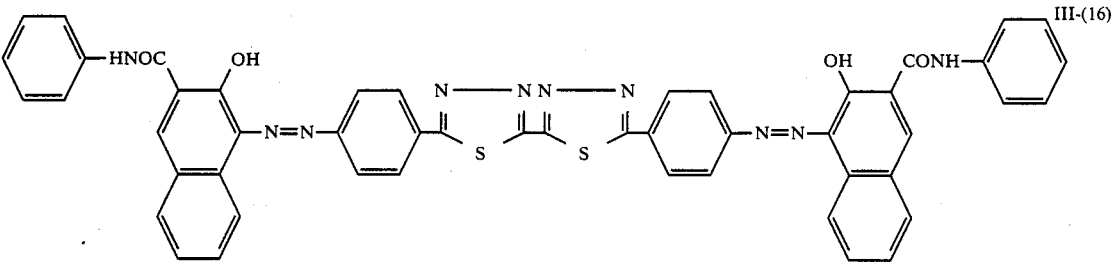
III-(16)

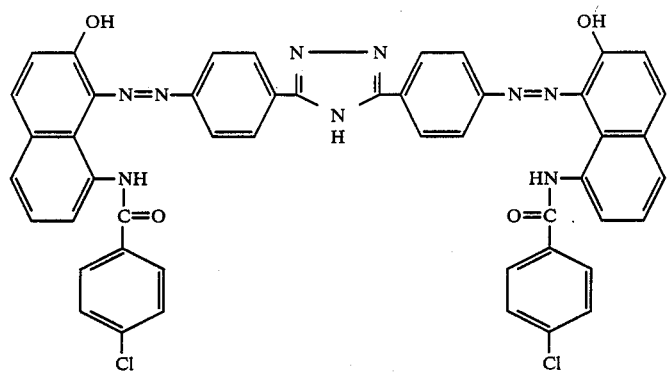
III-(17)
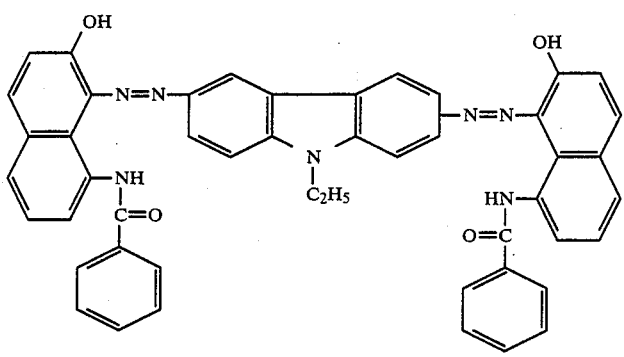
III-(18)
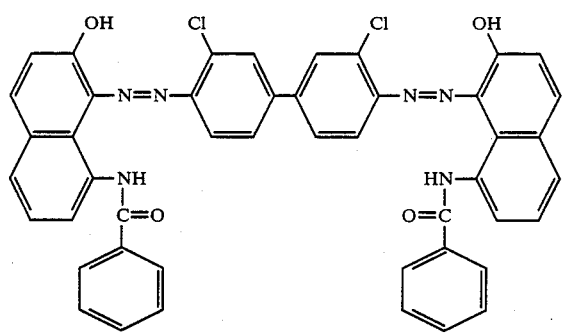
III-(19)
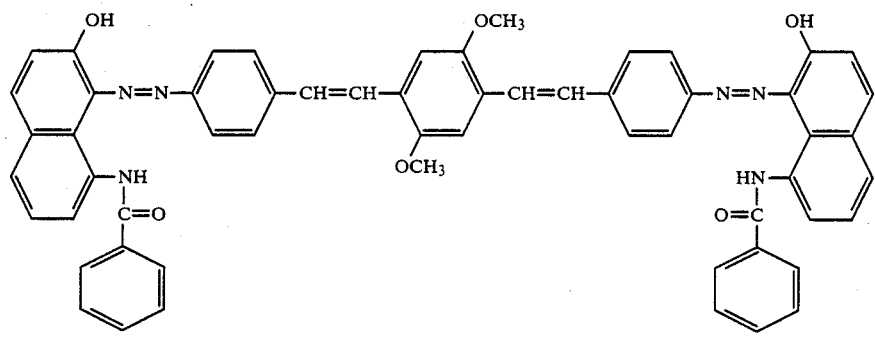
III-(20)

-continued
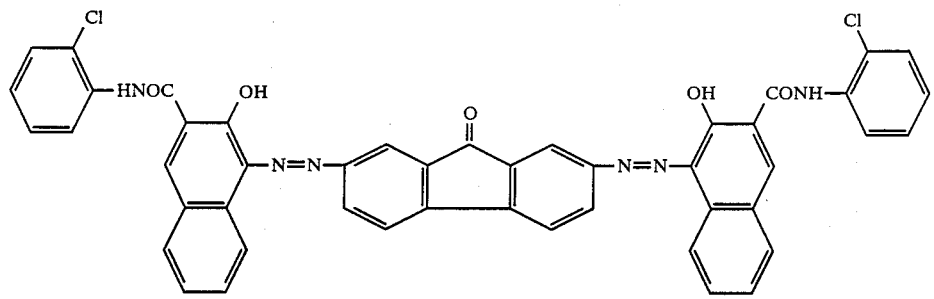
III-(21)
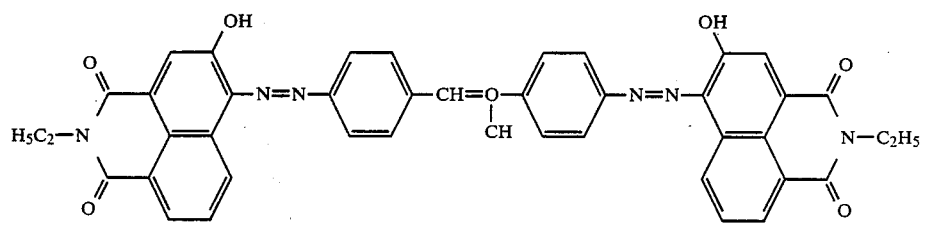
III-(22)
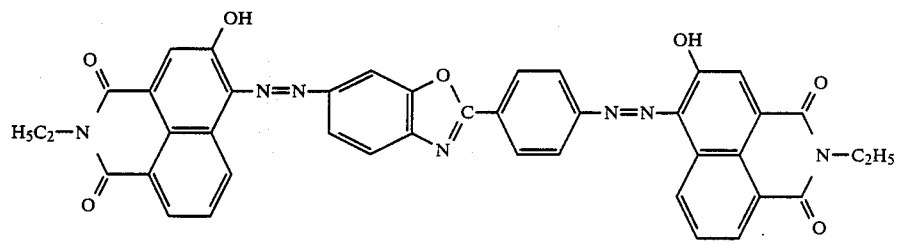
III-(23)
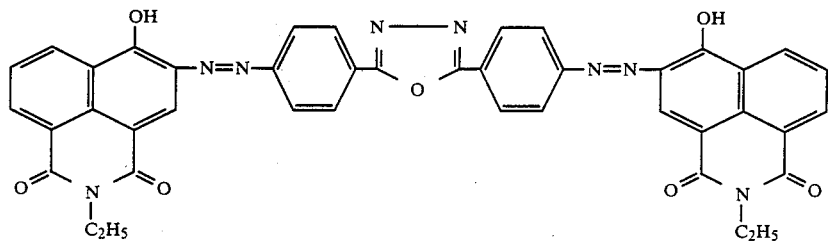
III-(24)
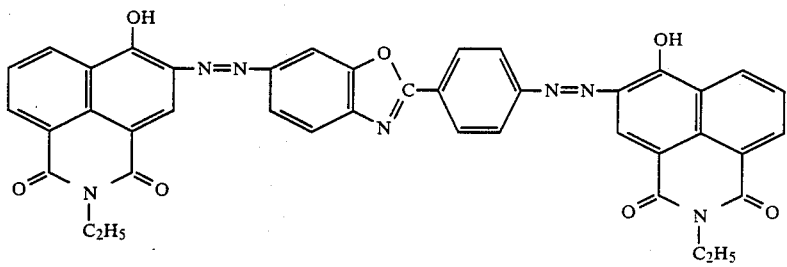
III-(25)
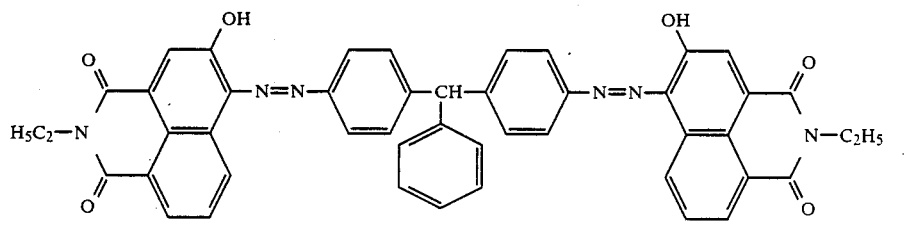
III-(26)

-continued
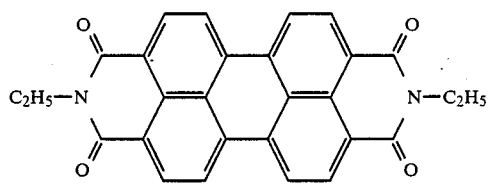
III-(27)
III-(28) Squalic acid methine dye
III-(29) Indigo dye (C.I. No. 78000)
III-(30) Thioindigo dye (C.I. No. 78800)
III-(31) B-type copper phthalocyanine
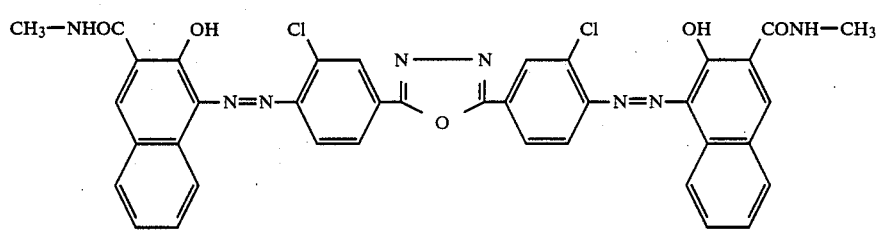
III-(32)
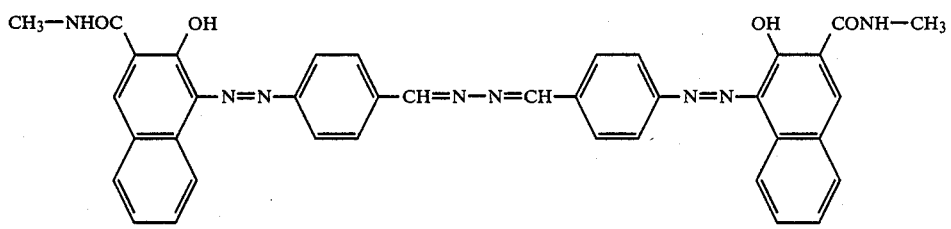
III-(33)
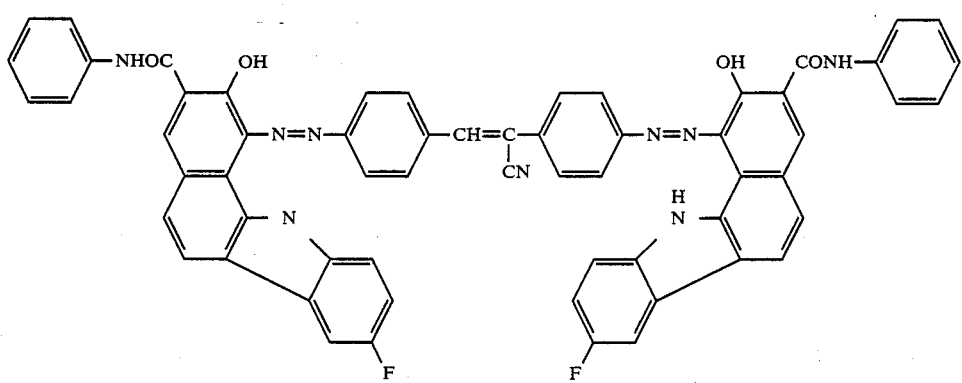
III-(34)
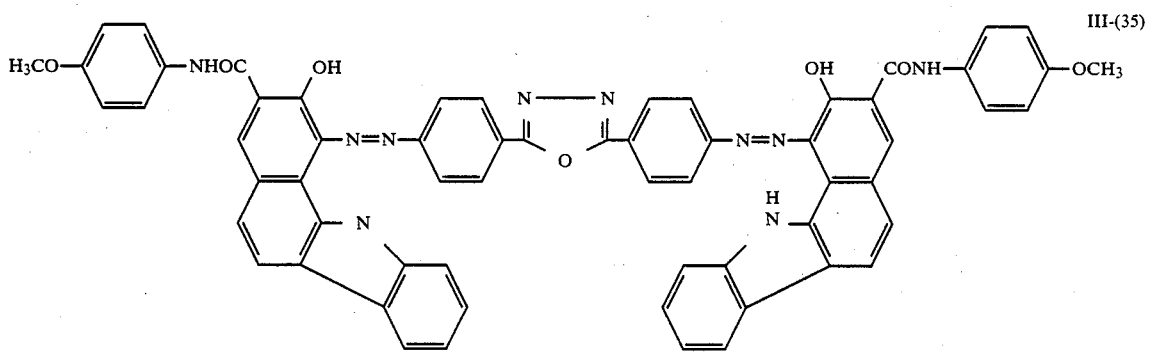
III-(35)

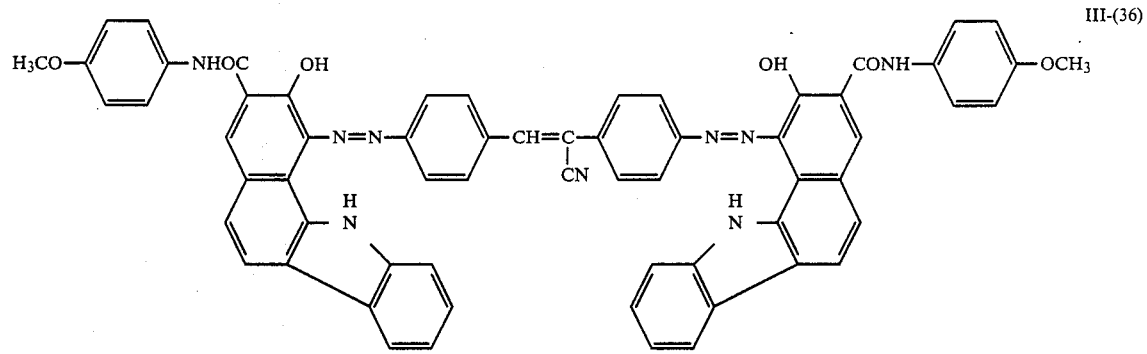
III-(36)
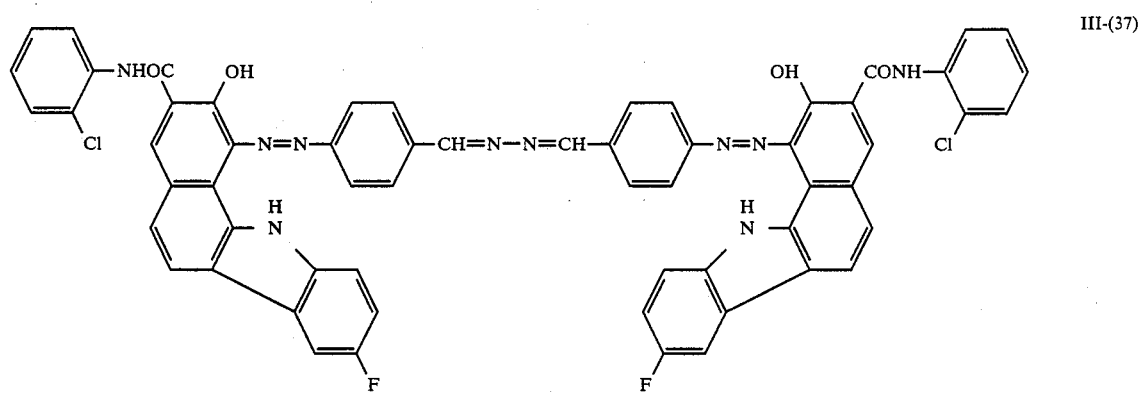
III-(37)
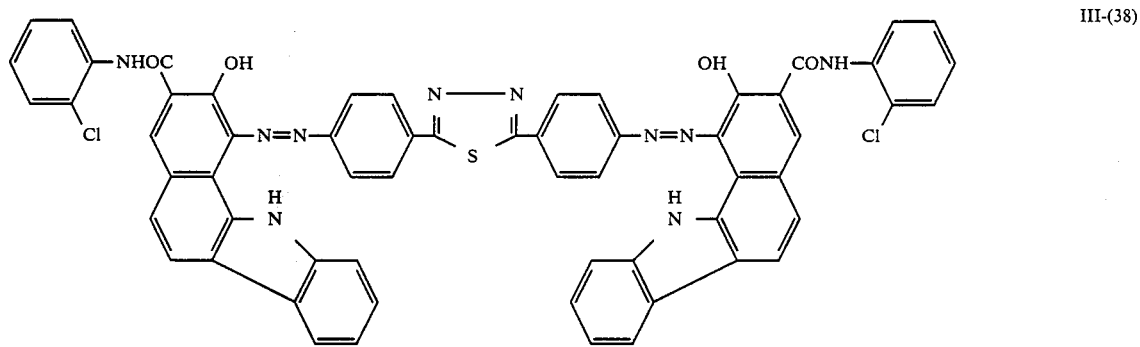
III-(38)
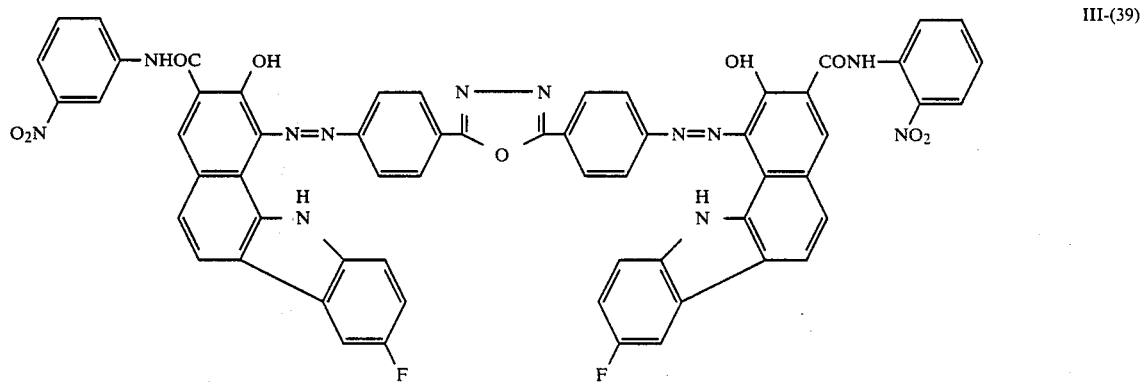
III-(39)

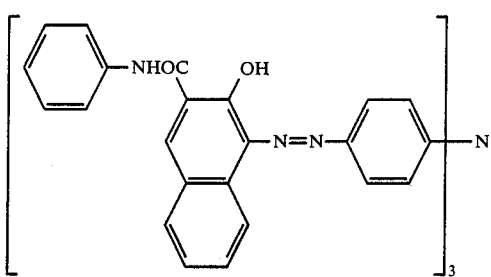
III-(40)
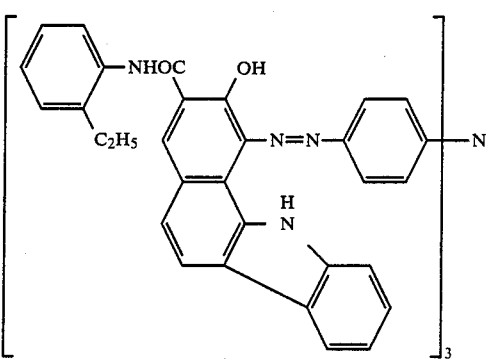
III-(41)
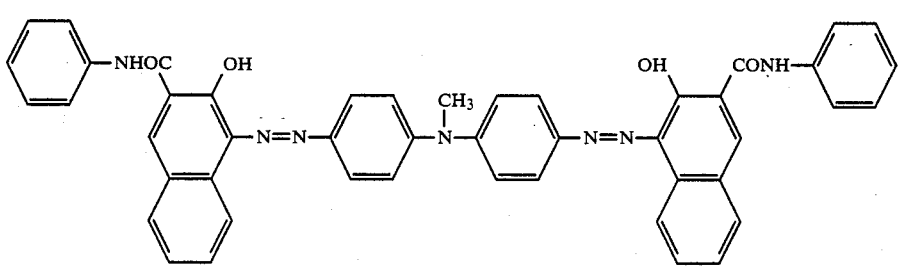
III-(42)
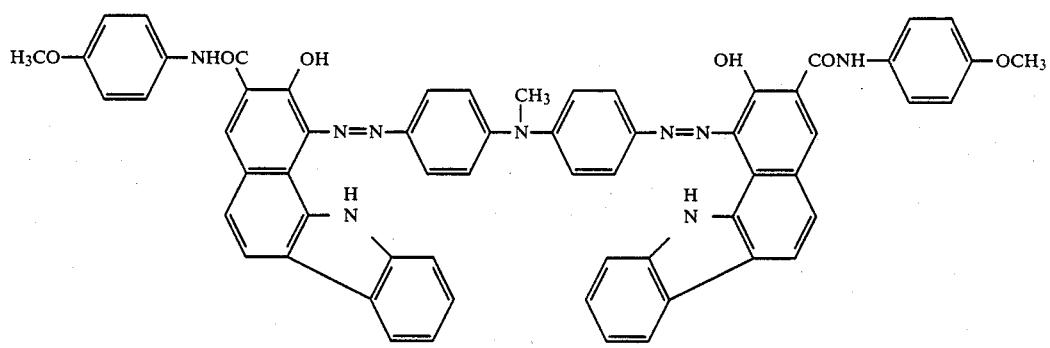
III-(43)
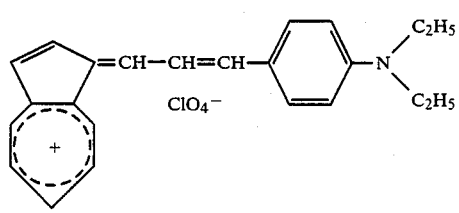
III-(44)

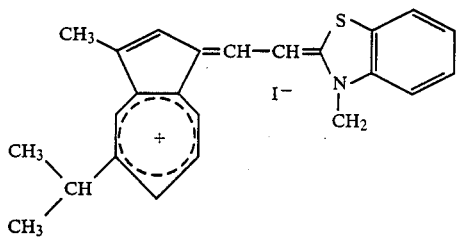

III-(45)

III-(46) 4-(4-dimethylaminophenyl)-2,6-diphenyl-thiapyrylium perchlorate

The charge generation layer can be formed by dispersing the above charge-generating material in a suitable binder and coating the resulting solution on a support, or can be obtained by forming a deposited film by using a vacuum deposition apparatus. The above binder can be selected from a vast range of insulating resins, and also can be selected from organic photoconductive polymers such as poly-N-vinyl carbazole, polyvinyl anthracene and polyvinyl pyrene. They may preferably include insulating resins such as polyvinyl butyral, polyacrylates (e.g., a condensation polymer of bisphenol A with phthalic acid, polycarbonates, polyesters, phenoxy resins, polyvinyl acetate, acrylic resins, polyacrylamides, polyamides, polyvinyl pyridine, cellulose resins, urethane resins, epoxy resins, casein, polyvinyl alcohol and polyvinyl pyrrolidone. The resin may suitably be contained in the charge generation layer in an amount of not more than 80% by weight, and preferably not more than 40% by weight. Usable as the organic solvent used in the coating are alcohols such as methanol, ethanol, isopropanol and the like, ketones such as acetone, methyl ethyl ketone, cyclohexane and the like, amides such as N,N-dimethylformamide, N,N-dimethylacetamide and the like, sulfoxides such as dimethylsulfoxide and the like, ethers such as tetrahydrofuran, dioxane, ethylene glycol monomethyl ether and the like, esters such as methyl acetate, ethyl acetate and the like, aliphatic halogenated hydrocarbons such as chloroform, methylene chloride, dichloroethylene, carbon tetrachloride, trichloroethylene and the like, or aromatics such as benzene, toluene, xylene, monochlorobenzene, dichlorobenzene and the like.

The coating can be carried out by using coating methods such as dip coating, spray coating, Meyer bar coating, blade coating and curtain coating.

The charge generation layer may preferably contain the above organic photoconductive material as much as possible in order to obtain a sufficient absorbance, and at the same time comprise a thin film layer, for example, a thin film layer having a film thickness of not more than 5 μm, and preferably from 0.01 to 1 μm, in order to shorten the flying course of the charge carriers generated. This is because a greater part of the amount of incident light is absorbed in the charge generation layer to produce a large number of charge carriers, and moreover the charge carriers generated must be injected into the charge transport layer without deactivation by recombination or trapping.

The photosensitive layer composed of a laminated structure comprising such a charge generation layer and charge transport layer is provided on a conductive support. Usable as the conductive support are those which the support itself is conductive, as exemplified by those made of aluminum, aluminum alloys, copper, zinc, stainless steel, vanadium, molybdenum, chromium, titanium, nickel, indium, gold, and platinum. Besides these, there can be also used plastics (as exemplified by polyethylene, polypropylene, polyvinyl chloride, polyethylene terephthalate, acrylic resins and polyethylene fluoride) having a layer formed into a film by vacuum deposition of aluminum, aluminum alloys, indium oxide, tin oxide, an indium oxide/tin oxide alloy and the like; supports comprising plastics or the above conductive support covered thereon with conductive particles (as exemplified by aluminum powder, titanium oxide, tin oxide, zinc oxide, carbon black and silver particles) together with a suitable binder; supports comprising plastics or paper impregnated with the conductive particles; and supports comprising plastics having conductive polymers.

A subbing layer having a barrier function and an adhesion function may be provided between the conductive support and photosensitive layer. The subbing layer can be formed by casein, polyvinyl alcohol, nitrocellulose, an ethylene/acrylic acid copolymer, polyamides (such as nylon 6, nylon 66, nylon 610, copolymer nylons, alkoxymethylated nylons and the like), polyurethanes, gelatin, aluminum oxide, etc.

The subbing layer may suitably have a film thickness of from 0.1 μm to 5 μm, and preferably from 0.5 μm to 3 μm.

In another embodiment of the present invention, the above disazo pigments, or the pigments or dyes having a photoconductivity, such as pyrylium dyes, thiapyrylium dyes, selenapyrylium dyes, benzopyrylium dyes, benzothiapyrylium dyes, naphthopyrylium dyes, naphthothiapyrylium dyes and the like, as disclosed in U.S. Pat. Nos. 3,554,745, 3,567,438, 3,586,500, etc. can be used also as sensitizers.

In still another embodiment, a eutectic complex of a pyrylium dye with an electrically insulating polymer having an alkylidene diarylene moiety, as disclosed in U.S. Pat. No. 3,684,502, etc., can also be used as a sensitizer. This eutectic complex can be obtained as a particulate eutectic complex by dissolving, for example, 4-[4-bis-(2-chloroethyl)aminophenyl]-2,6-diphenyl-thiapyrylium perchlorate and poly(4,4'-isopropylidene diphenylene carbonate) in a halogenated hydrocarbon solvent (as exemplified by dichloromethane, chloroform, carbon tetrachloride, 1,1-dichloroethane, 1,2-dichloroethane, 1,1,2-trichloroethane, chlorobenzene, bromobenzene and 1,2-dichlorobenzene), followed by addition thereto of a non-polar solvent (as exemplified by hexane, octane, decane, 2,2,4-trimethylbenzene and ligroin). The electrophotographic photosensitive member in this embodiment may contain a styrene/butadiene copolymer, a silicone resin, a vinyl resin, a vinylidene chloride/acrylonitrile copolymer, a styrene/acrylonitrile copolymer, a vinyl acetate/vinyl chloride copolymer, polyvinyl butyral, polymethyl methacrylate, poly- N-butyl methacrylate, polyesters, cellulose esters, and the like as a binder.

In a still another embodiment of the present invention, the photosensitive layer may not be limited to that of laminated structure of the function-separated type previously described, and there may be included an electrophotographic photosensitive member in which any of the particular amine compounds represented by the above general formulae is contained in the same photosensitive layer together with the charge-generating material.

The electrophotographic photosensitive member of the present invention is not only utilized in electrophotographic copying machines, but also can be widely used in the fields to which the electrophotography is applied, such as laser printers, CRT printers, and electrophotographic plate-making systems.

The present invention can give an electrophotographic photosensitive member having a high sensitivity, and also this electrophotographic photosensitive member has the advantage that it may suffer less potential fluctuation of light portion potential and dark portion potential when the charge and exposure to light are repeatedly carried out.

EXAMPLES

The present invention will be described below by giving Examples.

EXAMPLES 1 & 2

A coating solution was prepared by mixing 7 g of β-type copper phthalocyanine (trade name: Lionol Blue NCB Toner; produced by Toyo Ink Mfg. Co., Ltd.) fluxed in water, ethanol and benzene in this order followed by filtration to effect purification, 14 g of polyester [trade name: Polyester Adhesive 49000 (solid content: 20%); produced by DuPont Co.], 35 g of toluene and 35 g of dioxane, and dispersing the resulting mixture for 6 hours using a ball mill. This coating solution was coated on an aluminum sheet by Meyer bar coating so as to give a dried film thickness of 0.5 μm to form a charge generation layer.

Next, 7 g of the above exemplary compound I-1 as the charge-transporting material, and 7 g of a polycarbonate resin (trade name: Panlite K-1300; produced by Teijin Chemicals Ltd.) were dissolved in a mixed solvent comprising 35 g of tetrahydrofuran and 35 g of chlorobenzene, and the resulting solution was coated on the above charge generation layer by Meyer bar coating so as to give a dried film thickness of 16 μm to provide a charge transport layer, thus preparing an electrophotographic photosensitive member comprising a photosensitive layer of laminated structure.

The electrophotographic photosensitive member thus prepared was subjected to corona charging at −5 kV according to a static method using an electrostatic copy paper tester, Model-SP-428 manufactured by Kawaguchi Denki K.K., which was retained in the dark for 1 second and then exposed to light at an illumination of 2.5 lux.

The amount of exposure ($E_{\frac{1}{2}}$) necessary for decaying to ½ the surface potential ($V_0$) and the potential ($V_1$) after dark-decaying for 1 second was measured as the charging characteristics.

To further measure the fluctuation of light portion potential and dark portion potential after repeated use, the photosensitive member prepared in the present Example was stuck on a cylinder for a photosensitive drum of a PPC copying machine NP-150Z manufactured by Canon Inc. and the copying of 50,000 sheets was carried out using the same machine, to measure the fluctuation of light portion potential ($V_L$) and dark portion potential ($V_D$) observed at the initial stage and after the 50,000 sheet copying.

A photosensitive member was also prepared in the same manner but using the amine compound of the exemplary compound II-1 in place of the above exemplary compound, and the evaluation was similarly made.

Comparative samples No. 1 and No. 2 were also prepared in the same manner but using the amine compounds of the following structural formulas in place of the above exemplary compound, and the measurement was similarly made.

Comparative compound 1:

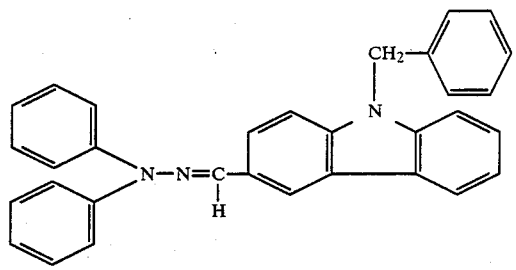

Comparative compound 2:

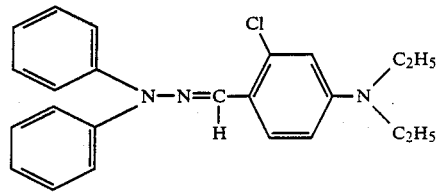

Results obtained are shown below in Table 1.

TABLE 1

| | $V_0$ (−V) | $V_1$ (−V) | $E_{\frac{1}{2}}$ (lux · sec) | Initial potential (−V) | After duration of 5,000 sheets (−V) |
|---|---|---|---|---|---|
| Example 1: | 700 | 680 | 1.8 | $V_D$: 660 $V_L$: 120 | 655 120 |
| Example 2: | 700 | 690 | 1.7 | $V_D$: 650 $V_L$: 120 | 640 120 |
| Comparative Example 1: | 680 | 630 | 3.1 | $V_D$: 650 $V_L$: 190 | 600 310 |
| Comparative Example 2: | 660 | 610 | 3.7 | $V_D$: 610 $V_L$: 230 | 580 350 |

As will be evident also from these results, the electrophotographic photosensitive members employing the compounds according to the present invention have a high sensitivity and also a superior duration stability.

EXAMPLES 3 to 18

In each Example, Example 1 was repeated but using the exemplary compound I-2, I-4, I-5, I-6, I-8, I-10, I-11, I-14, II-2, II-3, II-4, II-6, II-9, II-10, II-12 or II-14 in place of the exemplary compound I-1, and using the pigment of the exemplary compound III-(21) as the charge-generating material.

The electrophotographic performances of each photosensitive member were measured in the same manner as Example 1. Results obtained are shown below.

| Example | Exemplary compound | $E_{\frac{1}{2}}$ (lux·sec) | $V_0$ (−V) | $V_1$ (−V) |
|---|---|---|---|---|
| 3 | I-2 | 2.0 | 690 | 670 |
| 4 | I-4 | 2.7 | 690 | 680 |
| 5 | I-5 | 1.9 | 680 | 670 |
| 6 | I-6 | 2.2 | 700 | 690 |
| 7 | I-8 | 2.9 | 690 | 670 |
| 8 | I-10 | 2.5 | 700 | 680 |
| 9 | I-11 | 2.2 | 700 | 680 |
| 10 | I-14 | 2.3 | 680 | 670 |
| 11 | II-2 | 1.9 | 690 | 680 |
| 12 | II-3 | 2.2 | 680 | 660 |
| 13 | II-4 | 2.3 | 700 | 680 |
| 14 | II-6 | 2.3 | 700 | 680 |
| 15 | II-9 | 2.5 | 680 | 670 |
| 16 | II-10 | 1.7 | 700 | 690 |
| 17 | II-12 | 1.8 | 670 | 660 |
| 18 | II-14 | 2.6 | 710 | 690 |

| | Initial potential | | After duration of 50,000 sheets | |
|---|---|---|---|---|
| Example | $V_D$(−V) | $V_L$(−V) | $V_D$(−V) | $V_L$(−V) |
| 3 | 650 | 130 | 640 | 130 |
| 4 | 630 | 150 | 610 | 160 |
| 5 | 670 | 150 | 650 | 140 |
| 6 | 650 | 130 | 640 | 130 |
| 7 | 620 | 160 | 600 | 170 |
| 8 | 660 | 150 | 640 | 150 |
| 9 | 670 | 140 | 660 | 150 |
| 10 | 670 | 140 | 650 | 140 |
| 11 | 650 | 120 | 640 | 120 |
| 12 | 650 | 140 | 650 | 140 |
| 13 | 660 | 150 | 650 | 160 |
| 14 | 660 | 150 | 650 | 150 |
| 15 | 640 | 160 | 640 | 170 |
| 16 | 650 | 110 | 640 | 110 |
| 17 | 630 | 120 | 620 | 120 |
| 18 | 670 | 140 | 660 | 170 |

EXAMPLES 19 & 20

On an aluminum cylinder, an aqueous ammonium solution of casein (casein: 11.2 g; 28% ammonia water: 1 g; water 222 ml) was coated by dip coating, followed by drying to form a subbing layer with a coating weight of 1.0 g.m².

Next, 1 part by weight of a charge-generating material, the exemplary compound III-43, 1 part by weight of butyral resin (S-LEC BM-2; produced by Sekisui Chemical Co., Ltd.) and 30 parts by weight of isopropanol alcohol were dispersed for 4 hours using a ball mill dispersing machine. The resulting dispersion was coated by dip coating on the subbing layer previously formed, followed by drying to form a charge generation layer. This had a film thickness of 0.3 μm.

Next, 1 part of the above exemplary compound I-4 according to the present invention, 1 part by weight of polysulfone resin (P1700; produced by Union Carbide Corp.) and 6 parts by weight of monochlorobenzene were mixed and dissolved with stirring, using a stirrer. The resulting solution was coated on the charge generation layer by dip coating, followed by drying to form a charge transport layer. This had a film thickness of 20 μm.

Corona charging at −5 kV was carried out on the photosensitive member thus prepared, to measure the surface potential produced at this time (initial potential $V_0$). Further measured were the surface potential after the photosensitive members were left to stand in the dark for 5 second (attenuation). The sensitivity was evaluated by measuring the amount of exposure ($E_{\frac{1}{2}}$ μJ/cm²) necessary for decaying to $\frac{1}{2}$ the potential $V_k$ after dark-decaying for 1 second. In this occasion, a gallium/aluminum/arsenic three-component semiconductor laser (output: 5 mW; oscillation wavelength: 780 nm) was used as a light source.

Results obtained were as follows.
$V_0$: −700V
Potential retention ($V_k/V_0 \times 100$):96%
$E_{\frac{1}{2}}$:1.3 μJ/cm²

A photosensitive member was also prepared in the same manner except that the above exemplary compound was replaced with the exemplary compound II-5, and the evaluation was similarly made.

Results obtained were as follows.
$V_0$: −700V
Potential retention ($V_k/V_0 \times 100$):94%
$E_{178}$ :1.1 μJ/cm²

Next, the above photosensitive members were each set in a laser beam printer (LBP-CX, manufactured by Canon Inc.) which is a printer of a reversal development type electrophotographic system, equipped with the above semiconductor laser, to carry out tests of actual image formation. Conditions were as follows: Surface potential after primary charging: −700V; surface potential after imagewise exposure: −130V (the amount of exposure: 1.0 μJ/cm²); transfer potential: +700V; polarity of developer: negative; processing speed: 50 mm/sec.; development condition (developing bias): −450V; imagewise exposure scan system: image scanning; exposure to light before primary charging: red and whole-areal exposure of 50 lux·sec. Image formation was carried out by line-scanning the laser beam according to character signals and image signals, obtaining good prints in both characters and images.

EXAMPLES 21 & 22

In 100 ml of a toluene (50 parts by weight)/dioxane (50 parts by weight) solution of a polyester (Polyester Adhesive 49000, available from DuPont Co.), 3 g of 4-(4-dimethylaminophenyl)-2,6-diphenylthiapyrylium perchlorate and 5 g of the above exemplary compound I-9 were mixed, and the mixture was dispersed for 6 hours using a ball mill. The resulting dispersion was coated on an aluminum sheet by Meyer bar coating so as to give a film thickness of 15 μm after dried.

The electrophotographic performances of the photosensitive member thus prepared was measured in the same manner as Example 1. Results obtained are shown below.

$V_0$: −710V
$V_1$: −700V
$E_{\frac{1}{2}}$:2.3 lux·sec
Initial potential
$V_D$: −670V
$V_L$: −160V
After 50,000 sheet duration
$V_D$: −660V
$V_L$: −160V A photosensitive member was also prepared in the same manner except that the above exemplary compound was replaced with the exemplary compound II-12, and the evaluation was similarly made.

Results obtained are shown below.
$V_0$: −700V $V_1$: -690V
$E_{\frac{1}{2}}$: 2.0 lux·sec
Initial potential
$V_D$: -650V
$V_L$: -150V
After 50,000 sheet duration
$V_D$: -640V
$V_L$: -150V

EXAMPLES 23 & 24

On an aluminum sheet, an aqueous ammonium solution of casein (casein: 11.2 g; 28% ammonia water: 1 g; water 222 ml) was coated by Meyer bar coating, followed by drying to form an adhesion layer with a film thickness of 1 μm.

Next, 5 g of a disazo pigment having the following structural formula:

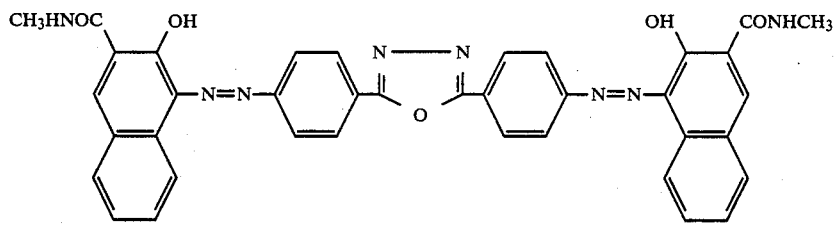

was dispersed together with a solution obtained by dissolving 2 g of butyral resin (degree of butyralization: 63 mol %) in 95 ml of ethanol, and thereafter the dispersion was coated on the adhesion layer to form a charge generation layer so as to give a film thickness of 0.4 μm after dried.

Next, a solution obtained by dissolving 5 g of the above exemplary amine compound I-13 and 5 g of poly-4,4'-dioxydiphenyl-2,2-propane carbonate (viscosity-average molecular weight: 30,000) in 150 ml of dichloromethane was coated on the charge generation layer, followed by drying to form a charge transport layer with a film thickness of 20 μm, thus preparing an electrophotographic photosensitive member.

The electrophotographic photographic characteristics of the electrophotographic photosensitive member thus prepared were measured in the same manner as Example 1.

Results obtained are shown below.
$V_0$: -690V
$V_1$: -670V
$E_{\frac{1}{2}}$: 2.2 lux·sec
Initial potential
$V_D$: -650V
$V_L$: -170V
After 50,000 sheet duration
$V_D$: -640V
$V_L$: -180V A photosensitive member was also prepared in the same manner except that the above exemplary compound was replaced with the exemplary compound II-9, and the evaluation was similarly made.

Results obtained are shown below.
$V_0$: -680V
$V_1$: -670V
$E_{\frac{1}{2}}$: 2.5 lux·sec
Initial potential
$V_D$: -630V
$V_L$: -180V
After 50,000 sheet duration
$V_D$: -620V
$V_L$: -190V

EXAMPLES 25 & 26

A molybdenum sheet (a substrate) of 0.2 mm thick, whose surface has been cleaned, was fixed on a given position in a glow discharge vapor deposition chamber. Next, the inside of the chamber was evacuated to a degree of vacuum of about $5 \times 10^{-6}$ Torr. Thereafter, the input voltage of a heater was raised and the temperature of the molybdenum substrate was maintained at 150° C. Then, hydrogen gas and silane gas (15% by volume based on hydrogen gas) were fed into the chamber, which was maintain at 0.5 Torr by regulating the gas flow rate and a main valve of the vapor deposition chamber. Next, a high frequency electric power of 5 MHz was applied to an induction coil to generate glow discharge in the internal part of the coil in the chamber, to provide an input electric power of 30W. Under the above conditions, an amorphous silicon film was made to grow on the substrate, and, after the same conditions were kept until the the film thickness reached 2 μm, the glow discharge was stopped. Thereafter, the heater and high frequency electric source were turned off; and, waiting until the substrate temperature fell to 10° C., flow-out valves of hydrogen gas and silane gas were closed. Then, the inside of the chamber was once brought to $10^{-5}$ Torr or less and thereafter restored to the atmospheric pressure to take out the substrate. Subsequently, on the resulting amorphous silicon layer, a charge transport layer was formed in entirely the same manner as Example 1 except that the exemplary compound I-3 was used as the charge-transporting material, thus preparing a photosensitive member.

A photosensitive member was also prepared in the same manner but using the exemplary compound II-2.

The photosensitive members thus prepared were set in a charge exposure experimental apparatus to carry out corona charging at ⊖6 kV, immediately followed by irradiation of a light image. The light image was irradiated through a test chart of a transmission type, using a tungsten lamp as a light source. Thereafter, a positively chargeable developer (containing toner and carrier) was immediately cascaded on the surfaces of the photosensitive members, thus obtaining good toner images on the surfaces of the photosensitive members.

EXAMPLES 27 & 28

In 200 ml of dichloromethane, 3 g of 4-(4-dimethylaminophenyl)-2,6-diphenylthiapyrylium perchlorate and 3 g of poly(4,4'-isopropylidenediphenylene carbonate) were thoroughly dissolved, followed by addition of 100 ml of toluene to precipitate a utectic complex. The resulting precipitate was filtered, followed by addition of dichloromethane to again effect dissolution, and then 100 ml of n-hexane was added in the resulting solution to obtain a precipitate of the utectic complex.

This utectic complex 5 g was added in 95 ml of methanol solution containing 2 g of polyvinyl butyral, and the mixture was dispersed for 6 hours using a ball mill. The resulting dispersion was coated by Meyer bar coating on an aluminum sheet having a casein layer, so as to give a film thickness of 0.4 μm after dried, to form a charge generation layer.

Next, on this charge generation layer, a cover layer of a charge transport layer was formed in entirely the same manner as Example 1 but using the exemplary compound I-10.

The photographic characteristics of the photosensitive member thus prepared were measured in the same manner as Example 1. Results obtained are shown below.

$V_0$: −690V
$V_1$: −670V
$E_{\frac{1}{2}}$: 2.7 lux·sec
Initial potential
$V_D$: −680V
$V_L$: −150V
After 50,000 sheet duration
$V_D$: −680V
$V_L$: −160V A photosensitive member was also prepared in the same manner except that the above exemplary compound was replaced with the exemplary compound II-10, and the evaluation was similarly made. Results obtained are shown below.

$V_0$: −700V
$V_1$: −690V
$E_{\frac{1}{2}}$: 2.2 lux·sec
Initial potential
$V_D$: −670V
$V_L$: −170V
After 50,000 sheet duration
$V_D$: −660V
$V_L$: −170V

EXAMPLES 29

In 150 ml of a tetrahydrofuran solution of polyester (Polyester Adhesive 49000; produced by DuPont Co.), 5 g of the same utectic compolex as the one used in Example 27 and 5 g of the above exemplary compound I-16 were added, and thoroughly mixed and stirred. The resulting solution was coated on an aluminum sheet by Meyer bar coating so as to give a film thickness of 15 μm after dried.

The photographic characteristics of the photosensitive member thus prepared were measured in the same manner as Example 1. Results obtained are shown below.

$V_0$: −700V
$V_1$: −680V
$E_{\frac{1}{2}}$: 2.7 lux·sec
Initial potential
$V_D$: −630V
$V_L$: −170V
After 50,000 sheet duration
$V_D$: −690V
$V_L$: −170V

I claim:

1. An electrophotographic photosensitive member comprising a conductive support and provided thereon a photosensitive layer, wherein said photosensitive layer contains an amine compound represented by the following Formula (I) or Formula (II)

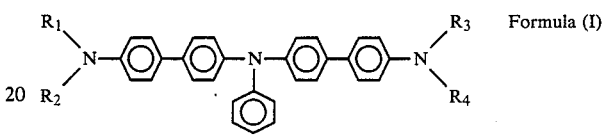

Formula (I)

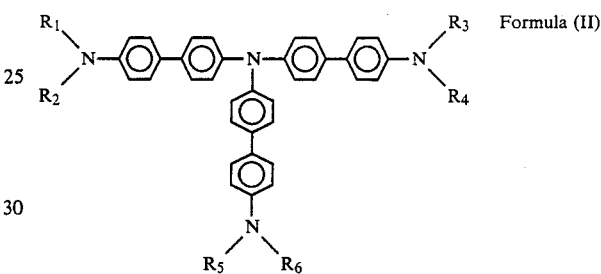

Formula (II)

wherein $R_1$, $R_2$, $R_3$, $R_4$, $R_5$ and $R_6$ each represent an alkyl group, an aralkyl group, or an aryl group.

2. The electrophotographic photosensitive member according to claim 1, wherein said amine compound is a charge-transporting material contained in the photosensitive layer.

3. The electrophotographic photosensitive member according to claim 1, wherein said photosensitive layer contains a charge-generating material.

4. The electrophotographic photosensitive member according to claim 1, wherein said photosensitive layer has laminated structure comprising a charge generation layer and a charge transport layer.

5. The electrophotographic photosensitive member according to claim 1, wherein said charge-generating material comprises an azo pigment or a phthalocyanine pigment.

6. The electrophotographic photosensitive member according to claim 1, wherein said photosensitive member comprises an intermediate layer between the conductive support and the photosensitive layer.

* * * * *